United States Patent [19]
Hirano et al.

[11] Patent Number: 5,976,175
[45] Date of Patent: Nov. 2, 1999

[54] FIBER OPTIC LASER CONDUCTING PROBE FOR PHOTODYNAMIC THERAPY

[75] Inventors: Toru Hirano, Hamamatsu; Akio Tanaka, Chiba; Masami Ohsawa, Hiki-gun; Takuya Kohno, Ohta-ku, all of Japan

[73] Assignees: Lederle (Japan), Ltd., Tokyo; Hamamatsu Photonics K.K., Hamamatsu; Moritex Corp., Tokyo, all of Japan

[21] Appl. No.: 08/666,674

[22] Filed: Jun. 18, 1996

[30] Foreign Application Priority Data

Jun. 26, 1995 [JP] Japan .................................. 7-192348

[51] Int. Cl.[6] ......................................... A61N 5/06
[52] U.S. Cl. .................. 607/89; 607/92; 606/2; 606/15; 606/16
[58] Field of Search .................. 607/88, 89, 90, 607/92, 93; 606/2, 15, 16, 17; 385/31, 901

[56] References Cited

U.S. PATENT DOCUMENTS

| 4,334,733 | 6/1982 | Takeshima et al. ................ 350/96.33 |
| 4,466,697 | 8/1984 | Daniel .................................. 350/96.33 |
| 4,986,628 | 1/1991 | Lozherko ................................ 607/88 |
| 5,530,780 | 6/1996 | Ohsawa .................................. 385/31 |

*Primary Examiner*—John P. Lacyk
*Assistant Examiner*—Rosiland Kearney
*Attorney, Agent, or Firm*—Wenderoth, Lind & Ponack, L.L.P.

[57] ABSTRACT

A fiber optic laser conducting probe is used for photodynamic therapy. In this fiber optic laser conducting probe, an optical fiber has an end used for conducting a pulse laser beam. The laser beam is conducted through the optical fiber and irradiated from the end. A end tip is made of polyamide resin. The end tip has a hollow portion, and is attached to the end of the optical fiber such that the pulse laser beam can be irradiated through the end of the optical fiber, through the hollow portion and through the end tip.

11 Claims, 5 Drawing Sheets

FIBER OPTIC LASER CONDUCTING PROBE FOR PHOTODYNAMIC THERAPY

BACKGROUND OF THE INVENTION AND PRIOR ART

The present invention relates to a fiber optic laser conducting probe used for therapy for an early cancer known as a photodynamic therapy.

Photodynamic therapy for an early cancer is performed, while observing the body cavity with an endoscope, by irradiating a laser beam in the amount as necessary against the affected part with a fiber optic laser and diffusion probe inserted through a forceps aperture of the endoscope. It is necessary to provide, at the extreme end of the probe, a tip capable of carrying out the irradiation of a laser beam in response to shapes of the body cavity, such as tubular organs such as the throat and cervical canal, and bag-like organs such as the stomach and lungs. For that purpose, methods heretofore proposed include U.S. Pat. No. 4,693,556 and U.S. Pat. No. 4,660,925, in which a tip is formed at the extreme end by an ultraviolet hardening resin containing a fine powder of quartz to provide a uniform diffusion of light; U.S. Pat. No. 4,676,231, in which a transparent liquid with suspended fine particles is put into a hollow transparent tip; and U.S. Pat. No. 4,649,151, which suggests in its specification and drawings that an epoxy resin mixed with light diffusion particles are coated on an internal surface of a hollow transparent tip.

Especially in case a pulse wave laser beam is used, an end tip formed of an inorganic material (Examples: quartz, sapphire, glass, etc.) tends to be easily cracked and broken, which is dangerous when the concentration and high densification of shock waves generated from a pulse laser occur in the tip. A situation tends to occur in a tip which uses hard plastics (Examples: polymethylmethacrylate resin, polystyrene resin, etc.) that causes the inner surface of the tip to be blackened to deteriorate the light irradiating performance.

On the other hand, a tip made of polyacetal resin known as Derlin (a trademark of Du Pont) has the possibility of generating formalin, which is injurious to the living body due to the thermal decomposition by the laser.

We have previously proposed, in Japanese Utility Model Application No. 75579/1993, an end tip made of polyolefin resin, particularly, polyethylene resin. No inconvenience occurred in the end tip according to this proposal when it was used under the conditions such that an excimer dye laser having a wavelength of 630 nm was caused to be incident as a pulse laser having an intensity of 4 mJ to 8 mJ/pulse at a frequency of 40 to 80 Hz from the fiber end so as to have an outgoing energy of 600 J in total from the end tip. However, in the end tip according to the above proposal, when it is used by causing the above-described laser to be incident from the fiber end with a laser intensity of 8 mJ/pulse or more at a frequency of 80 Hz or more, it was found that the tip becomes thermally softened, expanded or bent due to the rise in temperature caused by the heating of the laser, and a blackening phenomenon due to the generation of free carbon sometimes occurs.

It is natural that for relieving the pains of a patient during therapy or for increasing the efficiency of the medical treatment, an intense laser beam is rapidly applied to irradiate the same amount of irradiation in the shortest period of time. The end tip should be improved accordingly. On the other hand, the damage of end tip due to the rapid application of the laser beam, particularly damage that is injurious to the patient, should be completely avoided. The end tip for collecting or diffusing a pulse laser beam should be selected very carefully, unlike the end tip for a continuous wave laser.

SUMMARY OF THE INVENTION

It is an object of the present invention to provide a fiber optic laser conducting probe for photodynamic therapy which is stabilized in use even if a pulse wave laser beam having a high energy intensity is applied at a high repetitive frequency and which is high in safety.

The present invention has been developed as a result of various experiments and studies. According to a feature of the present invention, use is made, as materials for the end tip, of polycaprolactam known as nylon 6, polyhexamethyleneadipamide known as nylon 66, poly 11-aminododecanic acid known as nylon 11, and a polyamide resin such as poly 12-aminododecanic acid known as nylon 12.

The end tip made of a polyolefin resin such as polyethylene previously proposed by us poses no problem when a relatively low pulse laser energy is used. However, when a pulse laser beam at a high energy level is used, the end tip is denatured due to the energy, which is considered due to the short of the bonding force between molecules of polyolefin long chain molecules.

As a means for providing a strong high polymer molecule construction by increasing the bonding force between molecules, a van der Waals force of aromatic annuluses or a hydrogen bonding force of amido bonds can be used. In the case of the present invention, it has been found that use of an inter-force by the hydrogen bond between molecules of polyamide is most suitable.

More specifically, in the case where the polyamide resin of the present invention is used as a material for the end tip, when a pulse laser wave having an energy of 8 mJ/pulse or more, for example, is caused to be incident from the fiber end at a high repetitive frequency of 80 Hz or more, no inconvenience such as thermal softening, expansion, bending, foaming, etc. of the tip are found, despite the presence of a relatively large amount of laser irradiation as compared to the prior art. Further, the blackening phenomenon caused by the free carbon resulting from the cutting of bonds such as C—C, C—H, C—O, C—N, etc. due to the pulse shock energy which was of concern was found to be outside the problem, except for minor blackening in the case of an excessively large amount of laser energy irradiation.

The end tip of the fiber optic laser conducting probe made of nylon 6, nylon 66, nylon 610, nylon 11, nylon 12 or nylon copolymer can be manufactured by a cutting process from a stock block or by molding from a molten material. However, the molten material becomes transparent when it is rapidly cooled in a mold and can be used as a light conducting material such as a lens, prism or a mirror. On the other hand, the dimension of a molecular spherulite is increased to a size in excess of the wavelength of a laser beam caused by slow cooling from the molten material, annealing around the glass transition temperature of the material or wet-heat treatment to thereby scatter the laser beam of the wavelength. In this case, it can be used as a light diffusive tip material.

As described in the ensuing embodiments, the nylon resin has a feature in that it has a high durability of a pulse laser, and is a unique material that can be used for an end tip of a fiber optic laser device, as a transparent material used as an optical lens and prism, and as an opaque light diffusing material.

It is effective for increasing an outgoing amount of light in a direction as desired to provide a light reflecting mirror on the inner surface of a hollow portion of a tip. The effective means for scattering an outgoing light uniform include such that the inner surface of the tip is incised, that a clad at the end of the optical fiber within the tip is removed and exposed, and the surface thereof is roughened, and that the light outgoing end of a core is roughened.

These improved means will become apparent from the ensuing embodiments.

DESCRIPTION OF THE PREFERRED EMBODIMENTS

Figure 1:
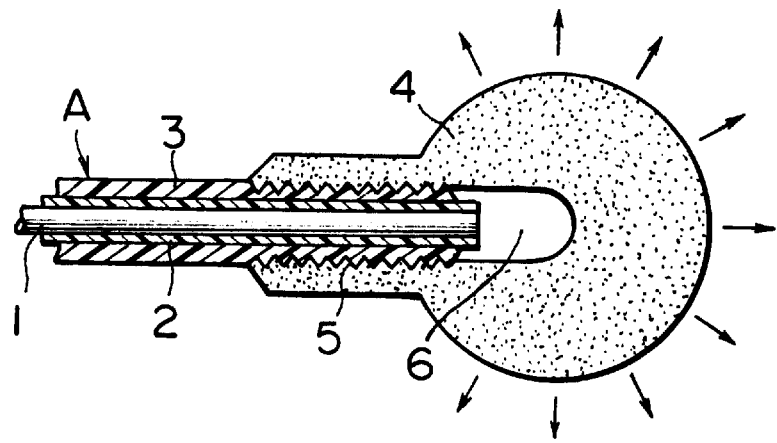
FIG. 1 is a sectional view of an embodiment of a whole directional light outgoing type device according to the present invention.

FIG. 1 shows an embodiment of a whole directional outgoing type device according to the present invention. As an optical fiber A, hard polymer cladded silica optical fiber, Toray Co., Ltd. HNS, FB400 (core diameter: 400 μmm) is used. Reference numeral 1 designates a core, 2 a plastic clad, 3 a plastic jacket, 4 a light diffusion tip made of polyamide resin, 5 a thread portion screwed between the plastic jacket 3 and the tip 4 and adhered and fixed by an epoxy resin, and 6 a hollow portion. The other end of the optical fiber, on which a pulse laser beam is incident, is not shown.

Figure 2:
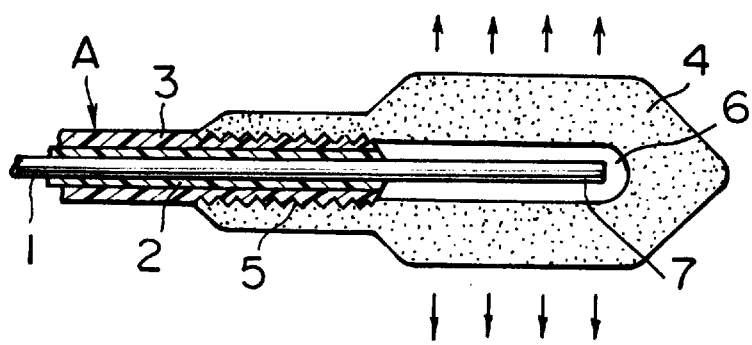
FIG. 2 is a sectional view of an embodiment of a side-directional light outgoing type device according to the present invention.

FIG. 2 shows an embodiment of a side-directional outgoing type device according to the present invention. The plastic clad at the extreme end of the optical fiber A is removed so that a core end 7 is exposed so as to increase the outgoing light.

Figure 3:
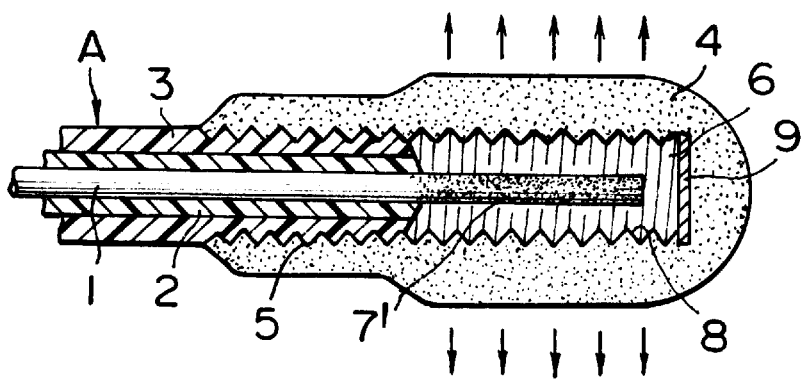
FIG. 3 is a sectional view of another embodiment of a side-directional light outgoing type device according to the present invention.

FIG. 3 shows another embodiment of a side-directional outgoing type device according to the present invention. The extreme end 7 of the core 1 with the plastic clad removed is subjected a sand blasting process to roughen the surface so as to make the outgoing light uniform. Reference numeral 8 designates an internal surface of a tip formed spirally for light diffusion, and 9 designates a light reflecting mirror.

Figure 4:
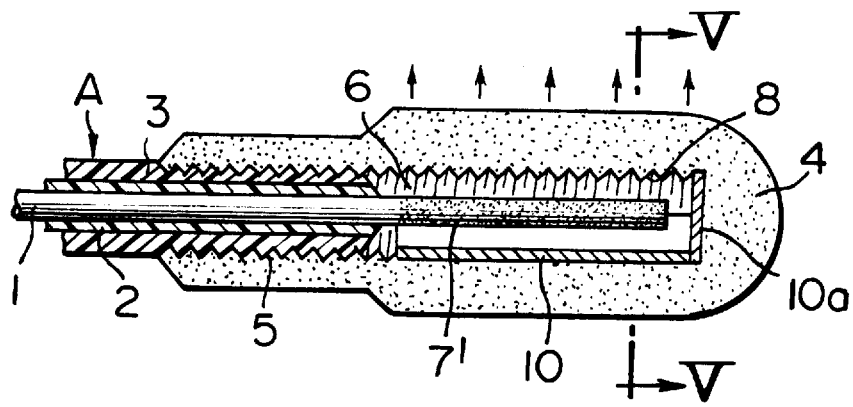
FIG. 4 is a sectional view of another embodiment of a side-directional light outgoing type device according to the present invention.
Figure 5:
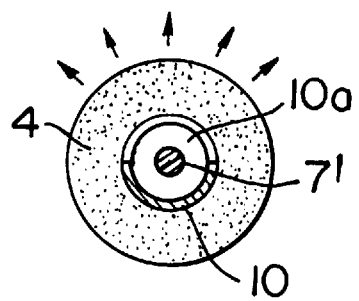
FIG. 5 is a sectional view taken on line V—V of FIG. 4.

FIGS. 4 and 5 shows another embodiment of a side-directional outgoing type device. There are provided a side portion of a core end 7' exposed and having its surface roughened, and a reflecting mirror 10 having an end part 10a on the inner surface of the tip 4. According to this embodiment, the amount of outgoing light can be further increased.

Figure 6:
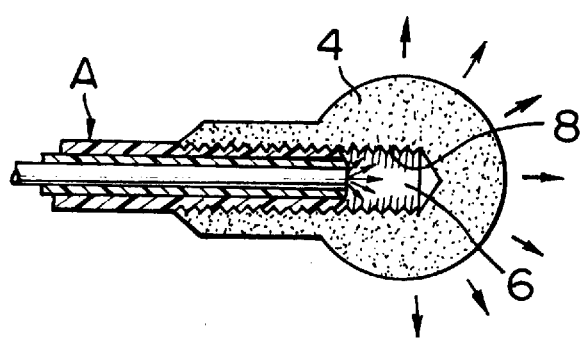
FIG. 6 is a sectional view of another embodiment of a whole directional light outgoing type device according to the present invention.
Figure 7:
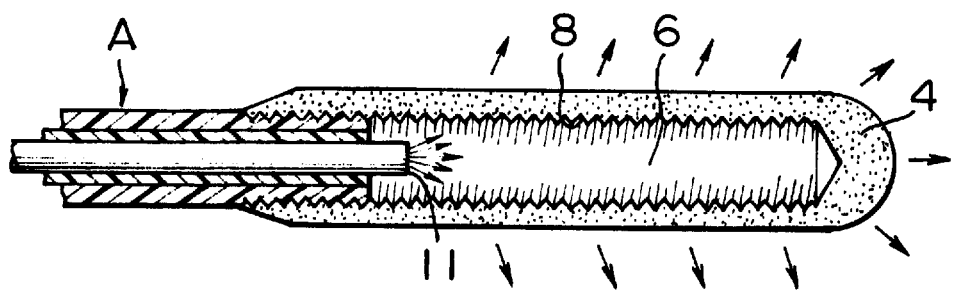
FIG. 7 is a sectional view of another embodiment of a side-directional light outgoing type device according to the present invention.

In FIGS. 6 and 7, the fiber end is roughened so as to make the outgoing light diffuse and uniform. FIG. 6 is a whole directional outgoing type device, and FIG. 7 is a side-directional outgoing type device.

In any of the above-described embodiments, the end tip made of polyamide resin has an external diameter of 1.5 to 2.0 mm, which is firmly secured to the FB 400 hard polymer cladded silica optical fiber, Toray Co., Ltd., as mentioned in the first embodiment.

In the embodiment of a whole directional outgoing type device shown in FIG. 1, the light diffusion tip 4 made of nylon 66 is attached to the optical fiber end. Normally, the outgoing irradiation is performed from the tip at about 200 J for 20 minutes under the laser incoming conditions of a 4 mJ/pulse and 40 Hz. However, here, the input into the conducting probe was performed with high energy, i.e., a laser input of an 8 mJ/pulse and 80 Hz at high frequency. In this case, it takes 20 minutes for the irradiation time under the normal conditions, whereas here, the same amount of laser energy can be irradiated in 5 minutes.

Figure 8:
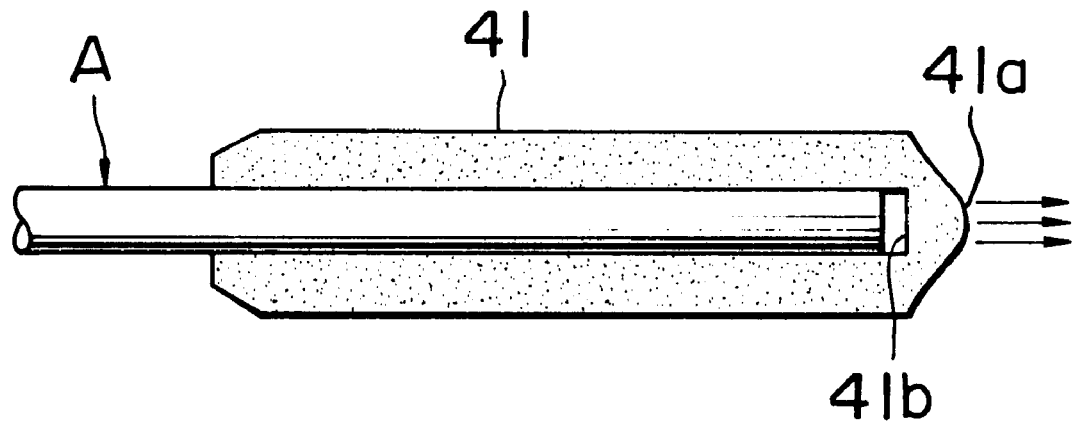
FIG. 8 is a sectional view of another embodiment of an end concentrated light outgoing type device using an end tip of a rapid-cool nylon 11 molded article.
Figure 9:
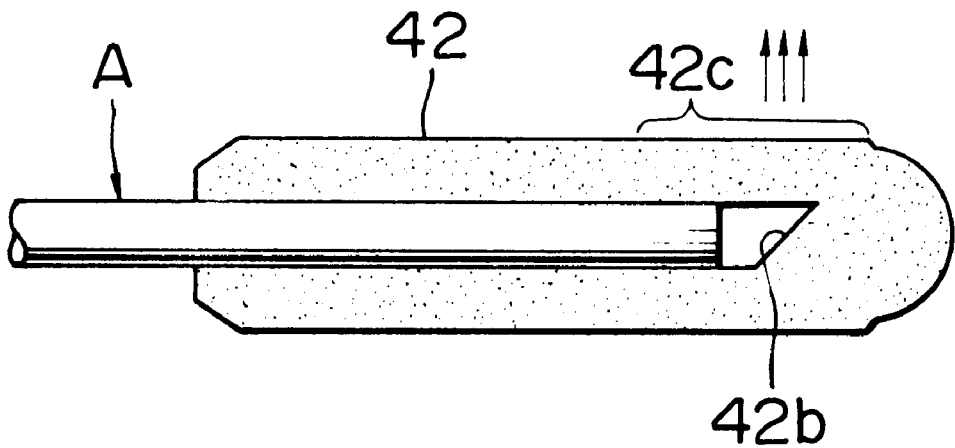
FIG. 9 is a sectional view of another embodiment of a side concentrated light outgoing type device using an end tip of a rapid-cool nylon 11 molded article.

FIGS. 8 and 9 shows another embodiment of a simple and practical laser device in which an end of the optical fiber A is inserted into, adhered and secured to a rapidly cooled nylon 11 molded article (end tips 41 and 42).

As previously mentioned, with the rapidly cooled nylon, the molded article is substantially transparent. Therefore, in the embodiment shown in FIG. 8, an end 41a in the form of a spherical surface functions as a convex lens integral with the tip so that the laser beam issued out of the end of the optical fiber A can be collected at a predetermined spot. The end 41a and an inner surface 41b are mirror-finished.

In the embodiment shown in FIG. 9, there is provided a laser device of the type in which an inner surface of the extreme end of the rapidly cooled nylon 11 molded article (end tip 42) is made to be an inclined surface of 45°, and an outer surface 42c opposed to the inner surface 42b is mirror-finished so that a laser beam issued out of the optical fiber A is reflected by the inner surface 42b, having the function of a reflecting mirror to direct it sideways.

Figure 10:
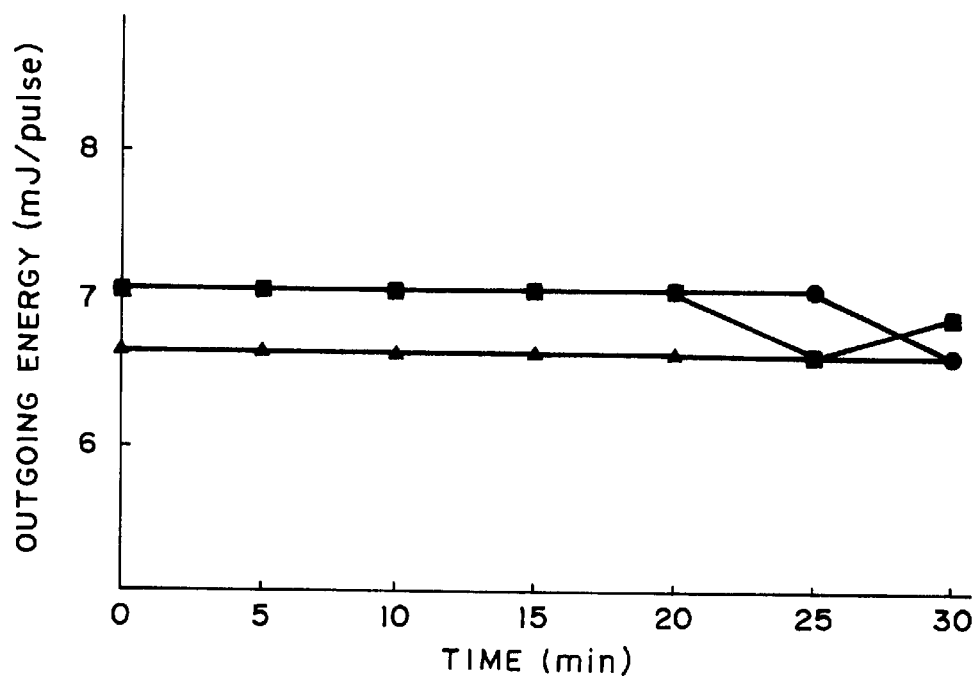
FIG. 10 is a graph showing a change in time of the intensity of outgoing laser energy from the end tip (mili-Joule/pulse) in the case where a light diffusion end tip of the construction shown in FIG. 1 is made of nylon 66 according to the present invention.

FIG. 10 shows the results of a test made on three probes having the construction shown in FIG. 1. It has been found that there is no problem in deterioration of the stability of the end tip made of nylon 66 under normal use conditions, even under the severe conditions as described.

Figure 11:
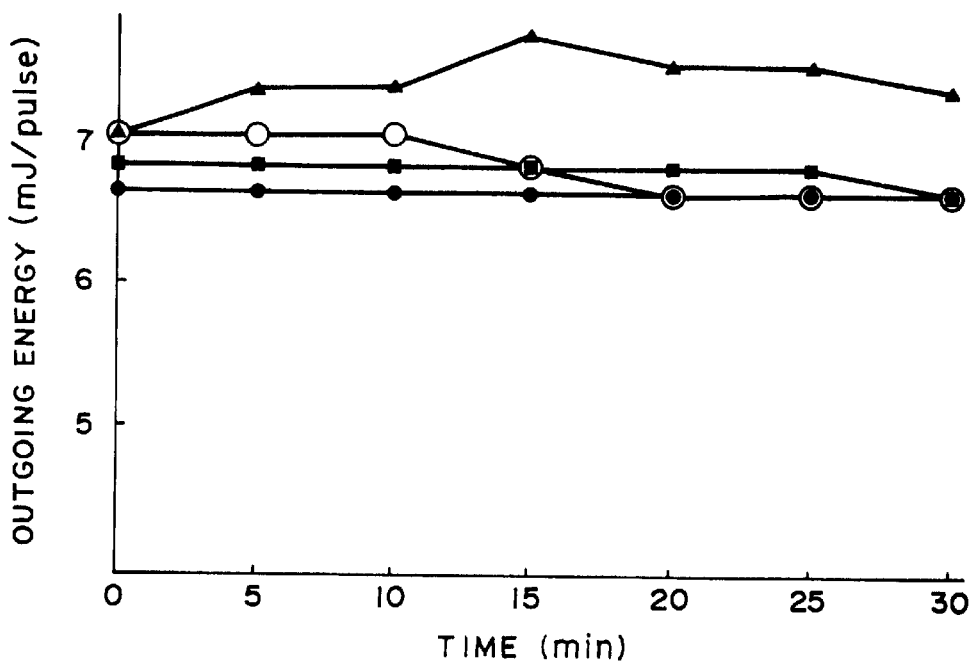
FIG. 11 is a graph showing a change in time of the intensity of outgoing laser energy from the end tip in the case where a light diffusion end tip of the construction shown in FIG. 7 is made of nylon 11 according to the present invention.

FIG. 11 shows the results of a test made on four products selected out of the end tips 4 having the construction shown in FIG. 7 according to the present invention, which are made of nylon 11 resin, showing a change in time of outgoing energy when the laser energy was allowed to pass through under exactly the same severe conditions as the case of FIG. 8. No deterioration occurs under normal use conditions for about 15 minutes, similarly to the previous embodiments. This property cannot be attained by the end tip made of other resins, which involves breakage, bending, foaming, inflation and the like due to the high temperature caused by the generation of heat.

Figure 12:
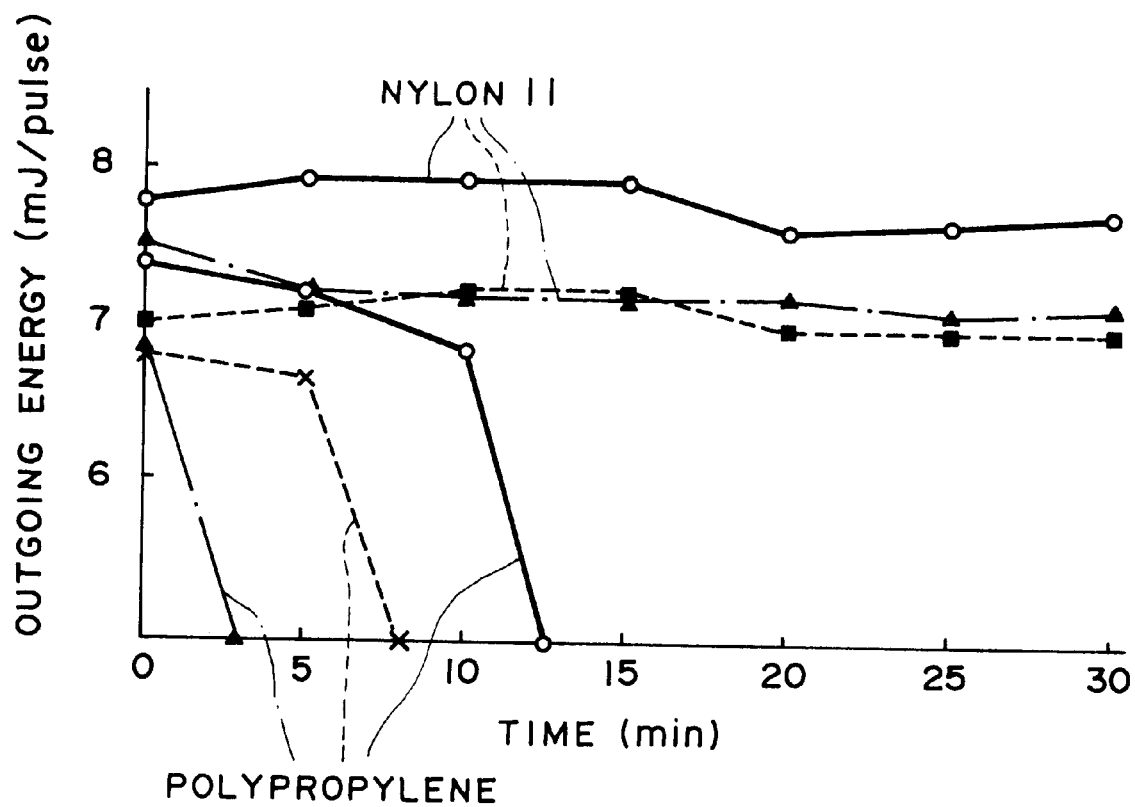
FIG. 12 is a comparison view showing the durability of the case where an end tip of the construction shown in FIG. 1 made of nylon 11 and the case where the end tip of the same construction as the former is made of polypropylene.

FIG. 12 is a graph showing the change in time of outgoing laser energies of the probe having the construction shown in FIG. 1 in which the end tip is made of nylon 11 and a probe having the same construction as the former in which an end tip is made of polypropylene. It is understood therefrom that the probe of the present invention made of nylon 11 is materially excellent in durability.

As described above, the polyamide resin known as nylon is used as the resin material for the light diffusion end secured to the end to manufacture the end tip. Thereby, even if a pulse laser wave of extremely higher energy than normal energy is passed at a high repetitive frequency, no abnormality occurs and as a result, the time required for therapy can be materially shortened. Accordingly, it is possible to provide a fiber optic laser conducting device used for the beam dynamic therapy for cancer known as a photodynamic therapy.

What is claimed is:

1. A fiber optic laser conducting probe for photodynamic therapy, comprising:

an optical fiber having an end for conducting a pulse laser beam through said optical fiber and irradiating the pulse laser beam from said end; and an end tip made of polyamide resin, said end tip having a hollow portion and being attached to said end of said optical fiber such that the pulse laser beam can be irradiated through said end of said optical fiber, said hollow portion, and said end tip.

2. The fiber optic laser conducting probe of claim 1, wherein said hollow portion of said end tip comprises a light reflecting mirror.

3. The fiber optic laser conducting probe of claim 1, wherein said end tip has an inner surface comprising a light reflecting portion.

4. The fiber optic laser conducting probe of claim 1, wherein said optical fiber comprises a core portion projecting into said hollow portion of said end tip, said core portion comprises a core end portion that is exposed in said hollow portion and that has a roughened surface.

5. The fiber optic laser conducting probe of claim 1, wherein said end tip has a portion thereof having a shape that defines a lens for collecting and diffusing the pulse laser beam.

6. The fiber optic laser conducting probe of claim 1, wherein said polyamide resin is one resin selected from the group consisting of nylon 11, nylon 12 and nylon 66, and wherein said end tip is a body selected from the group consisting of a transparent body formed by rapid cooling after molding from a melt and an opaque body formed by gradual cooling after molding from a melt.

7. The fiber optic laser conducting probe of claim 1, wherein said hollow portion is a space in said end tip extending between said end tip and said optical fiber.

8. The fiber optic laser conducting probe of claim 1, wherein said end tip comprises internal threads engaged with external threads on said optical fiber.

9. The fiber optic laser conducting probe of claim 1, wherein said end tip has internal threads defining said hollow portion.

10. The fiber optic laser conducting probe of claim 1, wherein said optic fiber comprises a core portion having a plastic clad, said optical fiber further comprising a core end portion extending into said hollow portion and free from said plastic clad.

11. The fiber optic laser conducting probe of claim 10, wherein said core end portion has a roughened surface.

* * * * *